(12) United States Patent
Poplawski et al.

(10) Patent No.: US 6,220,878 B1
(45) Date of Patent: *Apr. 24, 2001

(54) OPTOELECTRONIC MODULE WITH GROUNDING MEANS

(75) Inventors: Daniel S. Poplawski, Montgomery; Patrick B. Gilliland, Chicago; Alan J. Wallenberg, Villa Park, all of IL (US)

(73) Assignee: Methode Electronics, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/097,210

(22) Filed: Jun. 12, 1998

Related U.S. Application Data (63) Continuation of application No. 08/538,897, filed on Oct. 4, 1995, now Pat. No. 5,864,468.

(51) Int. Cl.$^7$ .................................................. H05K 5/00
(52) U.S. Cl. ................................................................ 439/92
(58) Field of Search ........................ 439/92, 95, 105, 439/108, 607; 365/92; 361/752, 753, 756, 802

(56) References Cited

U.S. PATENT DOCUMENTS

| | | | |
|---|---|---|---|
| Re. 32,502 | 9/1987 | Kumar | 439/92 |
| 2,899,669 | 8/1959 | Johanson . | |
| 3,264,601 | 8/1966 | Hartholz . | |
| 3,332,860 | 7/1967 | Diebold et al. . | |
| 3,474,380 | 10/1969 | Miller . | |
| 3,497,866 | 2/1970 | Patton, Jr. . | |
| 3,670,290 | 6/1972 | Angele et al. . | |
| 3,673,545 | 6/1972 | Rundle . | |
| 3,737,729 | 6/1973 | Carney | 317/101 PH |
| 3,792,284 | 2/1974 | Kaelin | 250/551 |
| 3,805,116 | 4/1974 | Nehmann | 317/99 |
| 3,809,908 | 5/1974 | Clanton | 250/217 |
| 3,976,877 | 8/1976 | Thillays | 250/227 |
| 4,149,072 | 4/1979 | Smith et al. | 250/199 |
| 3,990,761 | 11/1976 | Jayne . | |

(List continued on next page.)

FOREIGN PATENT DOCUMENTS

| | | |
|---|---|---|
| 4239124 A1 | 11/1992 | (DE) . |
| 0 228 278 | 12/1986 | (EP) . |
| 0 305112 A2 | 8/1988 | (EP) . |
| 0 314 651 A2 | 10/1988 | (EP) . |

(List continued on next page.)

OTHER PUBLICATIONS

AMP "PC Board Connectors" Product Catalog 82759 published Jun. 1991.
AMP Inc. "Lytel Molded–Optronic SC Duplex Transceiver" Dec. 1993 from Catalog 65922.
AMPHENOL Engineering News dtd Nov. 1994 vol. 7 No. 6.

(List continued on next page.)

Primary Examiner—Michael L. Gellner
Assistant Examiner—Daniel Wittels
(74) Attorney, Agent, or Firm—David L. Newman (57) ABSTRACT

A robust optoelectronic transceiver module which provides for static discharge and is quick, easy, and inexpensive to manufacture. The transceiver module has a main housing which consists of a potting box with potting material inserted therein. In addition, a circuit board is encased by the potting material. The circuit board has an optical subassembly mounted thereon. The optical subassembly extends outside of the potting box through a recess. Correspondingly, a recess cover is provided for forming a liquid tight seal between the recess cover, the potting box, and the optical subassembly. Furthermore, the module provides electrically conductive latches which are conductively connected, via tabs for forming an electrical connection, to a grounded structure, such as a computer chassis.

35 Claims, 4 Drawing Sheets

U.S. PATENT DOCUMENTS

| | | | |
|---|---|---|---|
| 4,156,903 | 5/1979 | Barton et al. | 340/172.5 |
| 4,161,650 | 7/1979 | Caoutte et al. | 250/199 |
| 4,176,897 | 12/1979 | Cameron . | |
| 4,217,019 | 8/1980 | Cameron | 339/40 |
| 4,217,488 | 8/1980 | Hubbard | 455/612 |
| 4,226,491 | 10/1980 | Kazoma et al. . | |
| 4,234,968 | 11/1980 | Singh | 455/607 |
| 4,249,266 | 2/1981 | Nakamori | 455/608 |
| 4,252,402 | 2/1981 | Puech et al. | 350/96.14 |
| 4,257,124 | 3/1981 | Porter et al. | 455/601 |
| 4,268,756 | 5/1981 | Crouse et al. | 250/551 |
| 4,273,413 | 6/1981 | Bendiksen et al. | 350/96.2 |
| 4,276,656 | 6/1981 | Petruk, Jr. | 455/608 |
| 4,294,682 | 10/1981 | Deczky | 204/244 |
| 4,295,181 | 10/1981 | Change et al. | 361/395 |
| 4,301,543 | 11/1981 | Palmer | 455/612 |
| 4,330,870 | 5/1982 | Arends | 455/617 |
| 4,345,808 | 8/1982 | Ingham | 339/40 |
| 4,347,655 | 9/1982 | Zory et al. | 29/589 |
| 4,357,606 | 11/1982 | Fortescue | 340/870.01 |
| 4,360,248 | 11/1982 | Bickel et al. | 350/96.16 |
| 4,366,565 | 12/1982 | Herskowitz | 370/1 |
| 4,369,494 | 1/1983 | Bienvenn et al. | 364/200 |
| 4,380,360 | 4/1983 | Parmer et al. | 339/17 CF |
| 4,388,671 | 6/1983 | Hall et al. | 361/383 |
| 4,393,516 | 7/1983 | Itani | 455/608 |
| 4,398,073 | 8/1983 | Botz et al. | 200/295 |
| 4,399,563 | 8/1983 | Greenberg | 455/607 |
| 4,408,273 | 10/1983 | Plow | 364/200 |
| 4,422,088 | 12/1983 | Gfeller | 357/19 |
| 4,427,879 | 1/1984 | Becher et al. | 250/215 |
| 4,430,699 | 2/1984 | Segarra et al. | 364/200 |
| 4,432,604 | 2/1984 | Schwab | 350/96.21 |
| 4,437,190 | 3/1984 | Rozenwaig et al. | 455/600 |
| 4,439,006 | 3/1984 | Stevenson | 350/96.2 |
| 4,446,515 | 5/1984 | Sauer et al. | 364/200 |
| 4,449,244 | 5/1984 | Kopainsky | 455/603 |
| 4,453,903 | 6/1984 | Pukoite | 425/117 |
| 4,459,658 | 7/1984 | Gabbe et al. | 364/200 |
| 4,461,537 | 7/1984 | Raymer, II et al. | 350/96.2 |
| 4,470,154 | 9/1984 | Yano | 455/607 |
| 4,486,059 | 12/1984 | DeYoung . | |
| 4,493,113 | 1/1985 | Forrest et al. | 455/606 |
| 4,501,021 | 2/1985 | Weizzq | 455/601 |
| 4,506,937 | 3/1985 | Cosmos et al. | 339/14 R |
| 4,510,553 | 4/1985 | Faultersack | 361/413 |
| 4,511,207 | 4/1985 | Newton et al. | 350/96.15 |
| 4,514,586 | 4/1985 | Waggoner | 174/35 |
| 4,516,204 | 5/1985 | Sauer et al. | 364/200 |
| 4,519,670 | 5/1985 | Spinner et al. | 350/96.15 |
| 4,519,672 | 5/1985 | Rogstadius | 350/96.2 |
| 4,519,673 | 5/1985 | Hamilton | 350/96.32 |
| 4,522,463 | 6/1985 | Schwenda et al. | 350/96.21 |
| 4,526,438 | 7/1985 | Essert | 350/96.2 |
| 4,526,986 | 7/1985 | Fields et al. | 549/254 |
| 4,527,286 | 7/1985 | Haworth | 455/601 |
| 4,529,266 | 7/1985 | Delebecque | 350/96.23 |
| 4,530,566 | 7/1985 | Smith et al. | 350/96.2 |
| 4,531,810 | 7/1985 | Carlsen | 350/96.2 |
| 4,533,208 | 8/1985 | Stowe | 350/96.16 |
| 4,533,209 | 8/1985 | Segerson et al. | 364/96.2 |
| 4,533,813 | 8/1985 | Rayburn et al. | 219/121 LH |
| 4,534,616 | 8/1985 | Bowen et al. | 350/96.2 |
| 4,534,617 | 8/1985 | Klootz et al. | 350/96.2 |
| 4,535,233 | 8/1985 | Abraham | 250/214 |
| 4,537,468 | 8/1985 | Begoix et al. | 350/96.21 |
| 4,539,476 | 9/1985 | Donuma et al. | 250/227 |
| 4,540,237 | 9/1985 | Winzer | 350/96.15 |
| 4,540,246 | 9/1985 | Fantone | 350/514 |
| 4,541,036 | 9/1985 | Landris et al. | 361/426 |
| 4,541,685 | 9/1985 | Anderson | 350/96.21 |
| 4,542,076 | 9/1985 | Bednarz et al. | 428/624 |
| 4,544,231 | 10/1985 | Peterson | 350/96.15 |
| 4,544,233 | 10/1985 | Iwamoto et al. | 350/96.2 |
| 4,544,234 | 10/1985 | Deveau, Jr. et al. | 350/96.21 |
| 4,545,074 | 10/1985 | Balliet et al. | 455/601 |
| 4,545,077 | 10/1985 | Drapala et al. | 455/612 |
| 4,545,642 | 10/1985 | Auracher et al. | 350/96.19 |
| 4,545,643 | 10/1985 | Young et al. | 350/96.2 |
| 4,545,644 | 10/1985 | DeVeau, Jr. et al. | 350/96.21 |
| 4,545,645 | 10/1985 | Mignien | 350/96.21 |
| 4,548,465 | 10/1985 | White | 350/96.2 |
| 4,548,466 | 10/1985 | Evans et al. | 350/96.2 |
| 4,548,467 | 10/1985 | Stoerk et al. | 350/96.21 |
| 4,549,782 | 10/1985 | Miller | 350/96.16 |
| 4,549,783 | 10/1985 | Schmachtenberg, III | 350/96.2 |
| 4,550,975 | 11/1985 | Levinson et al. | 350/96.18 |
| 4,553,811 | 11/1985 | Becker et al. | 350/96.2 |
| 4,553,813 | 11/1985 | McNaughton et al. | 350/96.2 |
| 4,553,814 | 11/1985 | Bahl et al. | 350/96.21 |
| 4,556,279 | 12/1985 | Shaw et al. | 350/96.15 |
| 4,556,281 | 12/1985 | Anderton | 350/96.2 |
| 4,556,282 | 12/1985 | Delebeque | 350/96.21 |
| 4,557,551 | 12/1985 | Dyott | 350/96.15 |
| 4,560,234 | 12/1985 | Shaw et al. | 350/96.15 |
| 4,563,057 | 1/1986 | Ludman et al. | 350/96.18 |
| 4,566,753 | 1/1986 | Mannschke | 350/96.16 |
| 4,568,145 | 2/1986 | Colin | 350/96.2 |
| 4,569,569 | 2/1986 | Stewart | 350/96.19 |
| 4,573,760 | 3/1986 | Fan et al. | 350/96.21 |
| 4,580,295 | 4/1986 | Richman | 455/618 |
| 4,580,872 | 4/1986 | Bhatt et al. | 350/96.16 |
| 4,588,256 | 5/1986 | Onstott et al. | 350/96.21 |
| 4,589,728 | 5/1986 | Dyott et al. | 350/96.3 |
| 4,595,839 | 6/1986 | Braun et al. | 250/551 |
| 4,597,631 | 7/1986 | Flores | 350/96.2 |
| 4,612,670 | 9/1986 | Henderson | 455/607 |
| 4,614,836 | 9/1986 | Carpenter et al. | 174/51 |
| 4,625,333 | 11/1986 | Takezawa et al. | 455/612 |
| 4,629,270 | 12/1986 | Andrews, Jr. et al. | 339/75 |
| 4,634,239 | 1/1987 | Buhrer | 350/486 |
| 4,641,371 | 2/1987 | Shutterly | 455/601 |
| 4,647,148 | 3/1987 | Katagiri | 350/96.2 |
| 4,652,976 | 3/1987 | Fushimoto | 361/393 |
| 4,663,240 | 5/1987 | Hajdu et al. | 428/545 |
| 4,663,603 | 5/1987 | Riemskijk et al. | 336/6 |
| 4,678,264 | 7/1987 | Bowen et al. | 350/96.2 |
| 4,679,883 | 7/1987 | Assini et al. | 439/607 |
| 4,695,106 | 9/1987 | Feldman et al. | 439/83 |
| 4,697,864 | 10/1987 | Hayes et al. | 439/444 |
| 4,708,433 | 11/1987 | Kakii et al. | 350/96.22 |
| 4,720,630 | 1/1988 | Takeuchi et al. | 250/227 |
| 4,722,584 | 2/1988 | Takii et al. | 350/96.2 |
| 4,727,248 | 2/1988 | Meur et al. | 250/239 |
| 4,737,008 | 4/1988 | Ohyama et al. | 350/96.2 |
| 4,756,593 | 7/1988 | Koakutsu et al. | 530/356 |
| 4,762,388 | 8/1988 | Tanaka et al. | 350/96.2 |
| 4,767,179 | 8/1988 | Sampson et al. | 350/96.2 |
| 4,772,931 | 9/1988 | Rogers | 357/3 |
| 4,789,218 | 12/1988 | Paul et al. | 350/96.21 |
| 4,798,430 | 1/1989 | Johnson et al. | 350/96.2 |
| 4,798,440 | 1/1989 | Hoffer et al. | 350/96.2 |
| 4,807,006 | 2/1989 | Rogers et al. | 357/3 |
| 4,807,955 | 2/1989 | Ashman et al. | 350/96.2 |
| 4,808,115 | 2/1989 | Norton et al. | 439/79 |
| 4,811,165 | 3/1989 | Currier et al. | 361/386 |
| 4,812,133 | 3/1989 | Fleak et al. | 439/248 |
| 4,821,145 | 4/1989 | Corfits et al. | 361/383 |
| 4,823,235 | 4/1989 | Suzuki et al. | 361/424 |
| 4,838,630 | 6/1989 | Jannson et al. | 350/3.7 |

| | | | | | | |
|---|---|---|---|---|---|---|
| 4,840,451 | 6/1989 | Sampson et al. . | | 5,170,146 | 12/1992 | Gardner ................. 338/313 |
| 4,844,581 | 7/1989 | Turner ................. 350/96.2 | | 5,183,404 | 2/1993 | Aldous et al. ................. 439/55 |
| 4,847,771 | 7/1989 | Inove ................. 364/431.05 | | 5,183,405 | 2/1993 | Elicker et al. ................. 439/108 |
| 4,849,944 | 7/1989 | Matsushita ................. 371/21 | | 5,195,911 | 3/1993 | Murphy ................. 439/607 |
| 4,857,002 | 8/1989 | Jensen et al. ................. 439/76 | | 5,202,943 | 4/1993 | Carden et al. ................. 385/92 |
| 4,872,736 | 10/1989 | Myers et al. ................. 350/96.2 | | 5,207,597 | 5/1993 | Kline et al. ................. 439/607 |
| 4,881,789 | 11/1989 | Levinson ................. 350/96.15 | | 5,212,752 | 5/1993 | Stephenson et al. ................. 385/78 |
| 4,884,336 | 12/1989 | Waters et al. ................. 29/845 | | 5,212,754 | 5/1993 | Basavanhally et al. ................. 385/90 |
| 4,897,711 | 1/1990 | Blonder et al. ................. 357/74 | | 5,218,519 | 6/1993 | Welch et al. ................. 361/415 |
| 4,906,197 | 3/1990 | Noll ................. 439/79 | | 5,225,760 | 7/1993 | Leiserson ................. 320/2 |
| 4,911,519 | 3/1990 | Burton et al. ................. 350/96.2 | | 5,233,676 | 8/1993 | Yonemura et al. ................. 385/88 |
| 4,912,521 | 3/1990 | Almquist et al. ................. 455/600 | | 5,234,353 | 8/1993 | Scholz et al. ................. 439/289 |
| 4,913,511 | 4/1990 | Tabalba et al. ................. 350/96.2 | | 5,238,426 | 8/1993 | Arnett ................. 439/557 |
| 4,927,225 | 5/1990 | Levinson ................. 350/96.18 | | 5,241,614 | 8/1993 | Ecker et al. ................. 385/94 |
| 4,945,229 | 7/1990 | Daly et al. ................. 250/227.11 | | 5,243,678 | 9/1993 | Schaffer et al. ................. 385/134 |
| 4,953,929 | 9/1990 | Basista et al. ................. 350/96.2 | | 5,247,532 | 9/1993 | Levinson ................. 372/38 |
| 4,969,924 | 11/1990 | Suverison et al. ................. 350/96.2 | | 5,259,052 | 11/1993 | Briggs et al. ................. 385/78 |
| 4,977,329 | 12/1990 | Eckhardt et al. ................. 250/551 | | 5,259,054 | 11/1993 | Benzoni et al. ................. 3895/89 |
| 4,979,787 | 12/1990 | Lichenberger ................. 350/96.2 | | 5,262,923 | 11/1993 | Batta et al. ................. 361/685 |
| 4,986,625 | 1/1991 | Yamada et al. ................. 350/96.2 | | 5,271,079 | 12/1993 | Levinson ................. 385/46 |
| 4,989,934 | 2/1991 | Zavracky et al. ................. 350/96.11 | | 5,274,729 | 12/1993 | King et al. ................. 385/134 |
| 4,990,104 | 2/1991 | Schieferly ................. 439/578 | | 5,280,191 | 1/1994 | Chang ................. 257/712 |
| 4,991,062 | 2/1991 | Kinhquoc ................. 361/424 | | 5,285,466 | 2/1994 | Tabatabaie ................. 372/50 |
| 5,004,434 | 4/1991 | Aiello et al. ................. 439/636 | | 5,285,511 | 2/1994 | Akkapeddi et al. ................. 385/89 |
| 5,005,939 | 4/1991 | Arvanitakis et al. ................. 350/96.2 | | 5,285,512 | 2/1994 | Duncan et al. ................. 385/94 |
| 5,006,286 | 4/1991 | Dery et al. ................. 264/40.2 | | 5,286,207 | 2/1994 | McHugh ................. 439/64 |
| 5,011,246 | 4/1991 | Corradetti et al. ................. 350/96.2 | | 5,288,247 | 2/1994 | Kaufman ................. 439/607 |
| 5,011,425 | 4/1991 | Van Zanten et al. ................. 439/353 | | 5,289,345 | 2/1994 | Corradetti et al. ................. 361/752 |
| 5,013,247 | 5/1991 | Watson ................. 439/55 | | 5,295,214 | 3/1994 | Card et al. ................. 385/92 |
| 5,019,769 | 5/1991 | Levinson ................. 372/31 | | 5,296,813 | 3/1994 | Holmes et al. ................. 324/322 |
| 5,029,254 | 7/1991 | Stickney ................. 175/35 GC | | 5,304,069 | 4/1994 | Brunker et al. ................. 439/108 |
| 5,035,482 | 7/1991 | Ten Berge et al. ................. 350/96.2 | | 5,305,182 | 4/1994 | Chen ................. 361/684 |
| 5,039,194 | 8/1991 | Block et al. ................. 383/88 | | 5,315,679 | 5/1994 | Baldwin et al. ................. 385/76 |
| 5,043,775 | 8/1991 | Lee ................. 357/19 | | 5,317,663 | 5/1994 | Beard et al. ................. 385/70 |
| 5,044,982 | 9/1991 | Bertini ................. 439/533 | | 5,321,819 | 6/1994 | Szczepanek ................. 395/325 |
| 5,045,971 | 9/1991 | Ono et al. ................. 361/386 | | 5,325,454 | 6/1994 | Rittle et al. ................. 385/76 |
| 5,046,955 | 9/1991 | Olsson ................. 439/74 | | 5,325,455 | 6/1994 | Henson et al. ................. 385/89 |
| 5,047,835 | 9/1991 | Chang ................. 357/74 | | 5,329,428 | 7/1994 | Block et al. ................. 361/785 |
| 5,060,373 | 10/1991 | Machura et al. ................. 29/858 | | 5,329,604 | 7/1994 | Baldwin et al. ................. 385/92 |
| 5,071,219 | 12/1991 | Yurtin et al. ................. 385/78 | | 5,333,221 | 7/1994 | Briggs et al. ................. 385/55 |
| 5,082,344 | 1/1992 | Mulholland et al. ................. 385/60 | | 5,333,225 | 7/1994 | Jacobowitz et al. ................. 385/93 |
| 5,084,802 | 1/1992 | Nguyenngoc ................. 361/424 | | 5,337,391 | 8/1994 | Lebby ................. 385/88 |
| 5,086,422 | 2/1992 | Hagiya et al. ................. 369/75.1 | | 5,337,396 | 8/1994 | Chen et al. ................. 385/92 |
| 5,091,991 | 2/1992 | Briggs et al. ................. 385/82 | | 5,337,398 | 8/1994 | Benzoni et al. ................. 385/90 |
| 5,093,879 | 3/1992 | Bregman et al. ................. 385/93 | | 5,345,524 | 9/1994 | Lebby et al. ................. 385/88 |
| 5,094,623 | 3/1992 | Scharf et al. ................. 439/607 | | 5,345,530 | 9/1994 | Lebby et al. ................. 385/88 |
| 5,099,307 | 3/1992 | Go et al. ................. 357/70 | | 5,353,364 | 10/1994 | Kurashima ................. 385/88 |
| 5,101,463 | 3/1992 | Cubukciyan et al. ................. 385/72 | | 5,353,634 | 10/1994 | Kurashima ................. 385/88 |
| 5,104,243 | 4/1992 | Harding ................. 385/84 | | 5,356,300 | 10/1994 | Costello et al. ................. 439/101 |
| 5,107,404 | 4/1992 | Tam ................. 361/424 | | 5,357,402 | 10/1994 | Anhalt . |
| 5,108,294 | 4/1992 | Marsh et al. ................. 439/76 | | 5,361,244 | 11/1994 | Nakamura et al. ................. 369/44.23 |
| 5,109,453 | 4/1992 | Edwards et al. ................. 385/90 | | 5,366,664 | 11/1994 | Varadan et al. ................. 252/512 |
| 5,113,466 | 5/1992 | Acarlar et al. ................. 385/88 | | 5,372,515 | 12/1994 | Miller et al. ................. 439/138 |
| 5,113,467 | 5/1992 | Peterson et al. ................. 385/88 | | 5,375,040 | 12/1994 | Cooper et al. ................. 361/730 |
| 5,116,239 | 5/1992 | Siwinski ................. 439/497 | | 5,383,793 | 1/1995 | Hsu et al. ................. 439/327 |
| 5,117,476 | 5/1992 | Yingst et al. ................. 385/88 | | 5,390,268 | 2/1995 | Morlion et al. ................. 385/59 |
| 5,118,362 | 6/1992 | St. Angelo et al. ................. 136/256 | | 5,397,242 | 3/1995 | Laisne et al. ................. 439/101 |
| 5,120,578 | 6/1992 | Chen et al. ................. 427/304 | | 5,398,154 | 3/1995 | Perkins et al. ................. 361/212 |
| 5,122,893 | 6/1992 | Tolbert ................. 359/152 | | 5,398,295 | 3/1995 | Chang et al. ................. 385/58 |
| 5,124,885 | 6/1992 | Liu ................. 361/391 | | 5,414,787 | 5/1995 | Kurata ................. 385/92 |
| 5,125,849 | 6/1992 | Briggs et al. ................. 439/378 | | 5,416,668 | 5/1995 | Benzoni ................. 361/816 |
| 5,127,071 | 6/1992 | Go ................. 385/73 | | 5,416,870 | 5/1995 | Chun et al. ................. 385/88 |
| 5,134,677 | 7/1992 | Leung et al. ................. 385/84 | | 5,416,871 | 5/1995 | Takahashi et al. ................. 385/88 |
| 5,134,679 | 7/1992 | Robin et al. ................. 385/90 | | 5,416,872 | 5/1995 | Sizer, II et al. ................. 385/92 |
| 5,136,063 | 8/1992 | Hasnain et al. ................. 372/50 | | 5,428,703 | 6/1995 | Lee ................. 385/78 |
| 5,136,152 | 8/1992 | Lee ................. 250/211 | | 5,428,704 | 6/1995 | Lebby et al. ................. 385/92 |
| 5,138,537 | 8/1992 | Wang ................. 362/187 | | 5,432,630 | 7/1995 | Lebby et al. ................. 359/152 |
| 5,138,678 | 8/1992 | Briggs et al. ................. 385/86 | | 5,434,747 | 7/1995 | Shibata ................. 361/753 |
| 5,140,663 | 8/1992 | Edwards et al. ................. 385/90 | | 5,446,814 | 8/1995 | Kuo et al. ................. 385/31 |
| 5,155,786 | 10/1992 | Ecker et al. ................. 385/94 | | 5,452,387 | 9/1995 | Chun et al. ................. 385/88 |
| 5,168,537 | 12/1992 | Rajasekharan et al. ................. 385/89 | | 5,452,388 | 9/1995 | Rittle et al. ................. 385/92 |

| | | | |
|---|---|---|---|
| 5,455,703 | 10/1995 | Duncan et al. | 359/152 |
| 5,463,532 | 10/1995 | Petitpierre et al. | 361/800 |
| 5,469,332 | 11/1995 | Alvite | 361/737 |
| 5,470,259 | 11/1995 | Kaufman et al. | 439/607 |
| 5,475,734 | 12/1995 | McDonald et al. | 379/58 |
| 5,475,783 | 12/1995 | Kurashima | 385/92 |
| 5,477,418 | 12/1995 | MacGregor et al. | 361/737 |
| 5,478,253 | 12/1995 | Biechler et al. | 439/181 |
| 5,479,288 | 12/1995 | Ishizuka et al. | 359/163 |
| 5,482,658 | 1/1996 | Lebby et al. | 264/1.24 |
| 5,487,678 | 1/1996 | Tsuji et al. | 439/352 |
| 5,491,712 | 2/1996 | Lin et al. | 372/50 |
| 5,494,747 | 2/1996 | Rha | 428/377 |
| 5,499,311 | 3/1996 | De Cusatis | 385/89 |
| 5,499,312 | 3/1996 | Hahn et al. | 385/91 |
| 5,515,468 | 5/1996 | DeAndrea et al. | 385/88 |
| 5,526,160 | 6/1996 | Watanabe et al. | 359/163 |
| 5,527,991 | 6/1996 | Sadowski et al. | 174/51 |
| 5,528,408 | 6/1996 | McGinley et al. | 359/152 |
| 5,534,662 | 7/1996 | Peacock et al. | 174/35 GC |
| 5,535,034 | 7/1996 | Taniguchi | 359/152 |
| 5,535,296 | 7/1996 | Uchida | 385/89 |
| 5,546,281 | 8/1996 | Poplawski | 361/752 |
| 5,547,385 | 8/1996 | Spangler | 439/101 |
| 5,548,641 | 8/1996 | Butler et al. | 379/399 |
| 5,548,677 | 8/1996 | Kakii et al. | 385/92 |
| 5,550,941 | 8/1996 | Lebby et al. | 385/49 |
| 5,554,031 | 9/1996 | Uleski | 439/76.1 |
| 5,561,727 | 10/1996 | Akita et al. | 385/88 |
| 5,567,167 | 10/1996 | Hayaski | 439/75 |
| 5,577,064 | 11/1996 | Swirhun et al. | 372/96 |
| 5,580,269 | 12/1996 | Fan | 439/79 |
| 5,588,850 | 12/1996 | Pan et al. | 439/92 |
| 5,596,663 | 1/1997 | Ishibashi et al. | 385/92 |
| 5,598,319 | 1/1997 | Lee | 361/684 |
| 5,599,595 | 2/1997 | McGinley et al. | 428/33 |
| 5,600,470 | 2/1997 | Walsh | 359/152 |
| 5,604,831 | 2/1997 | Dittman et al. | 385/88 |
| 5,613,860 | 3/1997 | Banakis et al. | 439/64 |
| 5,629,919 | 5/1997 | Hayashi et al. | 369/112 |
| 5,631,998 | 5/1997 | Han | 386/68 |
| 5,653,596 | 8/1997 | Banakis et al. | 439/64 |
| 5,659,459 | 8/1997 | Wakabayashia et l. | 361/753 |
| 5,675,428 | 10/1997 | Henmi | 359/161 |
| 5,687,267 | 11/1997 | Uchida | 385/89 |
| 5,717,533 | 2/1998 | Poplawski et al. | 361/752 |
| 5,724,729 | 3/1998 | Sherif et al. | 29/840 |
| 5,726,864 | 3/1998 | Copeland et al. | 361/800 |
| 5,734,558 | 3/1998 | Poplawski et al. | 361/752 |
| 5,736,782 | 4/1998 | Schairer | 257/679 |
| 5,747,735 | 5/1998 | Chang et al. | 174/51 |
| 5,767,999 | 6/1998 | Kayner | 359/163 |
| 5,779,504 | 7/1998 | Dominiak et al. | 439/709 |
| 5,864,468 | * 1/1999 | Poplawski et al. | 361/753 OR |
| 5,879,173 | 3/1999 | Poplawski et al. | 438/138 |

FOREIGN PATENT DOCUMENTS

| | | |
|---|---|---|
| 0 413 489 A2 | 6/1990 | (EP) . |
| 0 437 161 A2 | 11/1990 | (EP) . |
| 0 437 141 A2 | 12/1990 | (EP) . |
| 442 608 A2 | 8/1991 | (EP) . |
| 0 530 791 A2 | 9/1992 | (EP) . |
| 0 535 473 A1 | 9/1992 | (EP) . |
| 0 588 014 A2 | 7/1993 | (EP) . |
| 0 662 259 B1 | 9/1993 | (EP) . |
| 0 600 645 A1 | 11/1993 | (EP) . |
| 0 613 032 A2 | 2/1994 | (EP) . |
| 0 652 696 A1 | 2/1994 | (EP) . |
| 0 656 696 A1 | 2/1994 | (EP) . |
| 0 456 298 B1 | 2/1996 | (EP) . |
| 2 264 843 | 8/1993 | (GB) . |
| 2 288 939 A | 12/1994 | (GB) . |
| 61-158046 | 9/1986 | (JP) . |
| 61-188385 | 8/1987 | (JP) . |
| 63-009325 | 1/1988 | (JP) . |
| 63-16496 | 2/1988 | (JP) . |
| 63-65967 | 4/1988 | (JP) . |
| 63-65978 | 4/1988 | (JP) . |
| 63-82998 | 5/1988 | (JP) . |
| 1-237783 | 9/1989 | (JP) . |
| 2-87837 | of 1990 | (JP) . |
| 2-087837 | 3/1990 | (JP) . |
| 2-151084 | 6/1990 | (JP) . |
| 2-181710 | 7/1990 | (JP) . |
| 2-278212 | 11/1990 | (JP) . |
| 3-20458 | 1/1991 | (JP) . |
| 3-94869 | 4/1991 | (JP) . |
| 4-270305 | 4/1991 | (JP) . |
| 4-50901 | 2/1992 | (JP) . |
| 4-122905 | 4/1992 | (JP) . |
| 4-165312 | 6/1992 | (JP) . |
| 4-87809 | 7/1992 | (JP) . |
| 4-211208 | 8/1992 | (JP) . |
| 4-221207 | 8/1992 | (JP) . |
| 4-229962 | 8/1992 | (JP) . |
| 4-230978 | 8/1992 | (JP) . |
| 4-109593 | 9/1992 | (JP) . |
| 5-052802 | 3/1993 | (JP) . |
| 4-234715 | 5/1993 | (JP) . |
| 5-134147 | 5/1993 | (JP) . |
| 5-290913 | 5/1993 | (JP) . |
| 5-152607 | 6/1993 | (JP) . |
| 5-188250 | 7/1993 | (JP) . |
| 5-211379 | 8/1993 | (JP) . |
| 5-218581 | 8/1993 | (JP) . |
| 5-70955 | 9/1993 | (JP) . |
| WO 94/12900 | 11/1990 | (WO) . |
| WO 90/14607 | 6/1994 | (WO) . |

OTHER PUBLICATIONS

AT&T Microelectronics, "1408–Type ODL Transceiver-"Feb. 1994 preliminary data sheet.

Baldwin and Kellerman, "Fiber Optic Module Interface Attachment" Research disclosure Nov. 1991.

Block and Gaio "Optical Link Card guide/Retention Sys" Research Disclosures Apr. 1993.

Cinch Hinge Connectors Catalog CM–16, Jul. 1963.

Conductive Coatings by Dieter Gwinner.

Encapsulation of Electronic Devices and Components by Edward R. Salmon.

Hewlett–Packard Information for HP 5061–5800 Fiber Optic Interface converter including Declaration of Steve Joiner, Ph.D.

Hewlett–Packard Optoelectronics Designer's Catalog (1991–1992).

High Density Input/Output Connector Systems by Robert C. Herron.

IBM Technical Disclosure Bulletin dated Mar., 1987 vol. 29 No. 10.

IBM Fiber Channel 266 Mb/sOptical Link Cards.

James C. Pintner, Senior Attorney, Hewlett–Packard Company, letter dated Aug. 19, 1998.

Japanese Standards Association's "Japanese Industrial Standard F04 Type Connectors for Optical Fiber Cords JIS C 5973" 1990.

Methode Electronics letter to Leydig, Voit & Mayer, Ltd. from David L. Newman, dated Jun. 30, 1999.

Leydig, Voit & Mayer, Ltd. letter to Methode Electronics from Mark E. Phelps, dated Jun. 30, 1999.

Low Cost Fiber Physical Layer Medium Dependent Common Transceiver Footprint data sheet Jun. 23, 1992.
Siemens, "Low–Cost ATM" Advertisement.
Steve Joiner, Ph.D. Deposition Transcript and Exhibits dated May 12, 1998.
Sumitomo Electric Fiber Optics Corp. "Transceiver Manufacturers to Support Common Footprint for Desktop FDDI Applications," pre release and .
Headsup—Sumitomo Electric Lightwave joins other in announcement.
Sumitomo Electric Fiber Optics Corp Product Bulletin—FDDI Optical Transceiver.
Preliminary Bulletin FDDI Optical Transceiver Module—Sumitomo Electric.
Thomas & Betts Catalog 1988 for Info–Lan Modem.
Weik, "Communication Standard Dictionary" 1983 p. 454.
Vixel Corporation's Response Chart (Methode Electronics, Inc. v. Vixel Corporation. C98 20237 RMW EAI) Including explanation of 5,717,533 and 5,734,558 and citation of additional references; prepared Oct. 16, 1998.
Defendant Hewlett–Packard's Initial Disclosure of Prior Art Pursuant to Local Rule 16–7 Civil Action 99–04214 SBA ENE.
Defendant Finisar's Initial Disclosure of Prior Art Pursuant to Local Rule 16–7(e) Civil Action C 99–04214 SBA ENE.
Stackable Circuit Card Packaging with a Logic Cage IBM Technical Disclosure Bulletin, Dec. 1992.
5061–5800 Fiber Optic Interface Converter 1983 by Hewlett–Packard.
Info–Lan Modem Users Manual—Thomas & Betts, Aug. 1988.
Sumitomo Specifications ES9217–XC.
HP Module HFBR–5103, FDDI Data Sheet.
An optical Data Link using a CD laser.
CD laser optical Data Links for Workstation and Midrange Computers.
Minimizing Electrostatic Discharge to a Cartridge.
Raylan Joins Low–Wavelength Push –850 nm Transceiver.
Thomas & Betts INFO LAN Transceiver User Manual.
BCP, Inc. 305 East Drive, Suite A, Melbourne, FL 32904, USA, Technical Article . . . .
IBM, OptoElectronci Enterprise, Oct. 1992 ANSI Meeting A Performance for . . . .
IBM OptoElectronics Enterprise: RCL–2000 LCF–PMDL: Preliminary . . . .
IBM Technical Disclosure Bulletin "Optical Link Card Guide/Retention System".
Who provides Low–Cost Transceivers for all Standards?Siemens, undated.
Sumitomo Electric Fiber Optics Corp., Transceiver Manufacturers to Support . . . .
FDDI Low–Cost Fiber Phyiscal Layer Medium Dependent (LCF–PMD) . . . .
FDDI 1300nm Transceiver; Technical Data HFGR–5125.
Infineon Technologies, Corporation's Initial Disclosure of Prior Art; Lawsuit No. C 99 21142, United States District Court Northern District of California,.
Defendant Optical Communication Products, Inc.'s Initial Disclosure of Prior Art Pursuant to Civil L.R. 16–7(d)–(e).

* cited by examiner

OPTOELECTRONIC MODULE WITH GROUNDING MEANS

This application is a continuation of U.S. Ser. No. 08/538,897 filed Oct. 4, 1995 now U.S. Pat. No. 5,864,468.

BACKGROUND OF THE INVENTION

This invention relates generally to optoelectronic transceiver modules and in particular, it relates to an optoelectronic transceiver module, and its method of manufacture, whereby the module is inexpensive to manufacture, has a small yet robust package, provides for static discharge, and can be installed and replaced via a ribbon style connector.

Optoelectronic transceiver modules provide for the bidirectional transmission of data between an electrical interface and an optical data link. The module receives electrically encoded data signals which are converted into optical signals and transmitted over the optical data link. likewise, the module receives optically encoded data signals which are converted into electrical signals and transmitted onto the electrical interface.

Normally, the transceiver is mounted onto one of the circuit card assemblies of a host computer, input/output system, peripheral device, or switch. Therefore, as with all electronic equipment, there is a need for a transceiver having an outer package design which occupies as little circuit card surface area as possible.

In addition, there is a need for a transceiver module which is highly reliable and durable. One method presently used to ensure reliability and durability is to encapsulate the electronics of the transceiver within an insulative potting material. Encapsulating the transceiver electronics results in reducing vibration sensitivity and prevents unauthorized personnel from meddling with the module's electronics.

Presently, the molding of the potting material around the transceiver electronics is performed by placing the electronics within a silicone mold. Any portion of the electronics which extends outside of the mold is caulked, by hand, with a silicone compound which provides for a liquid tight seal. Once the mold is sealed, potting material is inserted therein. After the potting material is allowed to cure, the silicone mold is peeled away from the newly formed module.

The above described prior art molding process has several drawbacks. For example, it is time consuming and results in a transceiver module which has a pitted outer surface. In addition, the silicone mold used in the molding process has a limited life of only three to five modules before a new mold must be employed.

The optoelectronic module is provided with a plurality of electrical pins for forming an electrical connection with a circuit card assembly. The electrical pins consist of solid wire strands with each pin having one end connected to the electronics within the module and the other end protruding from the module's potting material.

The portion of each pin which protrudes from the potting material is either soldered within a plated through-hole, which is provided by the circuit card assembly, or placed within a connector which grasps onto the pin. However, the flimsy wire pins are very susceptible to deformation during both the normal handling of the module and its removal and installation onto a circuit card assembly. Thus, the flimsy pins currently used in the prior art are difficult and time consuming to attach to a circuit card assembly since they must be periodically inspected and realigned. Furthermore, the pins may break if they are realigned too many times.

In addition to the electrical pins, the module also is equipped with two mounting ports for physically securing the module onto the circuit card assembly. The module is placed onto the circuit card assembly so that the mounting ports align with holes provided in the circuit card assembly. Once the module is properly aligned, screws are inserted through the holes in the circuit card assembly and into the mounting ports of the module. The screws are then tightened until the module is firmly affixed to the circuit card assembly.

Similarly, to remove the module from the circuit card assembly, the screws must be removed and the wires either unsoldered from the circuit card or pulled from the connector which is a timely and expensive process requiring multiple components.

Finally, once the module is secured to the circuit card assembly, optical fibers contained within an SC duplex plug connector are mated to the module. Normally, the SC duplex connector has a plastic housing which may be statically charged. Thus, its connection onto the transceiver module may result in damage to the electronic components within the module unless proper grounding of the SC connector is provided.

It should be appreciated by those skilled in the art that the possibility of damage due to static discharge is not only applicable to transceiver modules which mate with an SC duplex connector. Other optoelectronic modules, such as, for example, Gigabaud Link Modules (GLM), are also susceptible to static discharge damage whenever they are mated to a connector containing optical fibers.

Therefore, there is a need for a transceiver module which provides for a small, yet robust package, which is inexpensive to manufacture, provides for static discharge, and can easily and quickly be installed and removed from a circuit card assembly. The present invention is such an apparatus.

Likewise, there is a need for preventing a statically charged fiber optic connector from damaging the electronics within an optoelectronic module.

In view of the above, it is an object of the present invention to provide a small transceiver module package.

It is another object of the present invention to provide a module package that has a robust and tamper resistent design.

Also, it is an object of the present invention to provide a module which can quickly be installed and replaced from a circuit card assembly.

Another object of the present invention is to provide a module package design that can quickly and easily be produced.

A further object of the present invention is to provide a module package that can be produced inexpensively.

It is yet another object of the present invention to prevent a statically charged connector from damaging the electrical circuitry within an optoelectronic module by pre-grounding the plug connector.

Furthermore, it is an object of the present invention to provide a module with a coating which dissipates an electrostatic discharge and serves as an electromagnetic shield.

SUMMARY OF THE INVENTION

In one form of the invention, a robust optoelectronic transceiver module is provided which is quick, easy, and inexpensive to manufacture. The transceiver module has a main housing which consists of a potting box with potting material inserted therein. In addition, a circuit board is encased by the potting material.

The invention further provides for an optical subassembly to be mounted on a circuit board. In addition, the potting box has a recess which allows the optical subassembly to extend outside of the potting box. Furthermore, a recess cover may be provided for forming a liquid tight seal between the recess cover, the potting box, and the optical subassembly.

The optoelectronic transceiver module may also have a ribbon style connector attached to the circuit board and protruding from the main housing. The ribbon style connector may protrude from either the bottom or one end of the main housing. In addition, the ribbon style connector may comprise of either a male ribbon style connector or a resilient male ribbon style connector.

In another form of the invention, an optoelectronic transceiver module is provided which mounts onto a circuit card assembly. The module has a main housing with a bottom. Protruding from the bottom of the main housing is a ribbon style connector which allows for quickly installing and replacing the module from the circuit card assembly.

In yet another form of the invention, a method of assembling an optoelectronic transceiver module is provided. The steps of the method consists of placing a circuit board within a potting box and injecting potting material within the potting box. In addition, the circuit board may be affixed within the potting box after the circuit board is positioned within the potting box. Furthermore, a liquid tight recess cover may be mounted within the potting box's recess after the circuit board is positioned within the potting box.

Also, the method of manufacture provides for coating the potting box with a conductive metal before the circuit board is placed within the potting box or after the potting material is injected within the potting box. Moreover, a connector shell may be mounted onto the potting box after the potting material is injected within the potting box.

In still another form of the invention, a method of assembling an optoelectronic transceiver is provided which includes the steps of affixing a circuit board within a housing and securing a conductive metal coating onto the housing.

In another form of the invention, a potting box is provided for potting optoelectronic components which include an optical subassembly. The potting box includes a wall having a recess which allows the optical subassembly to extend outside of the potting box. In addition, a recess cover is provided for forming a liquid tight seal between the recess cover, the potting box, and the optical subassembly. Furthermore, the invention provides for the potting box to have a standoff column for mounting a circuit board within the potting box and an alignment guide for engaging a groove within the recess cover.

In yet another form of the invention, an optoelectronic module is provided for mounting within a grounded structure, such as a computer chassis. The optoelectronic module consists of electrically conductive latches which are conductively connected to a structure which provides for the forming of an electrical connection with the grounded structure. The optoelectronic transceiver module may further include a transceiver connector attached thereto and which is conductively connected to the latches. Furthermore, a grounding clip may be attached to the transceiver connector. The grounding clip may have at least one tab extending therefrom. Accordingly, the optoelectronic module may use at least one tab for conductively connecting the latches to the grounded structure.

Various means for practicing the invention and other advantages and novel features thereof will be apparent from the following detailed description of an illustrative preferred embodiment of the invention.

BRIEF DESCRIPTION OF THE DRAWINGS

There is shown in the drawings a preferred embodiment of the present invention, wherein like numerals in the various figures pertain to like elements, and wherein.

DETAILED DESCRIPTION OF THE PRESENTLY PREFERRED EMBODIMENTS

Figure 1:
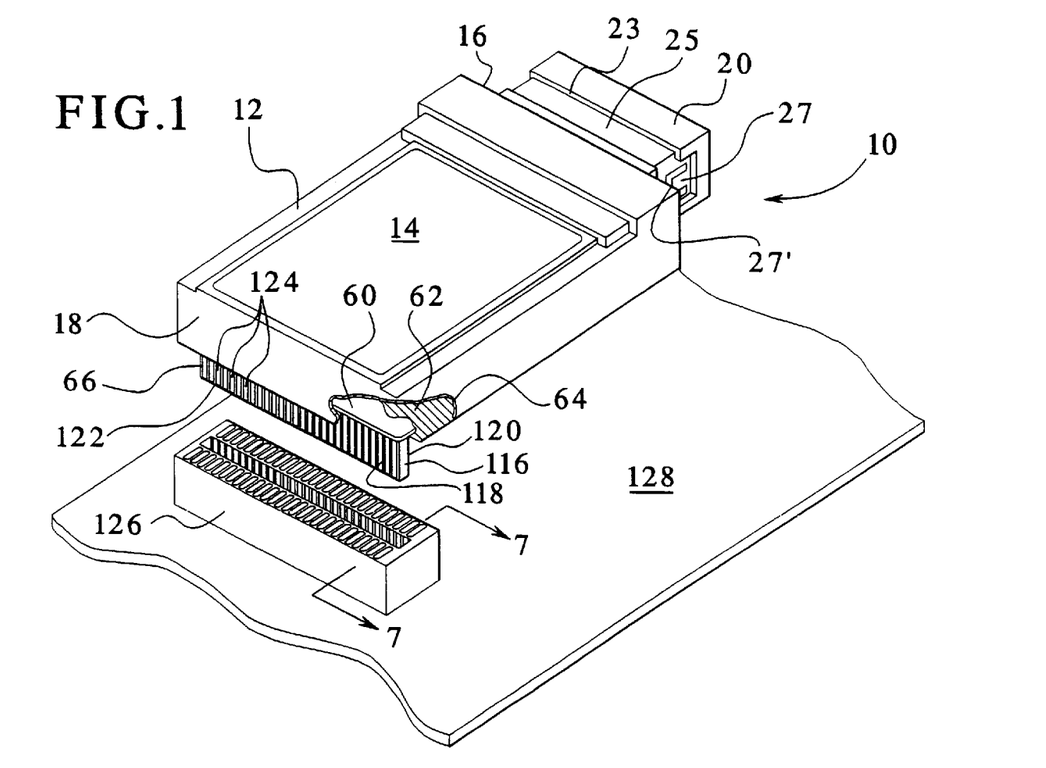
FIG. 1 is an enlarged perspective view of an optoelectronic transceiver module in accordance with the present invention and having a partial fragmentary view depicting the module's circuit board and potting material.

Referring to the drawings, and particularly to FIG. 1, an enlarged perspective view of an optoelectronic transceiver module 10 in accordance with the present invention is depicted. The module 10 has a main housing 12 which generally has the shape of an oblong box. The main housing 12 has a generally rectangular top 14 with a first end 16 and an opposite second end 18 extending perpendicularly from the top. Attached to the first end 16 of the main housing 12 is a transceiver connector 20 for receiving fiber optic plugs.

Figure 2:
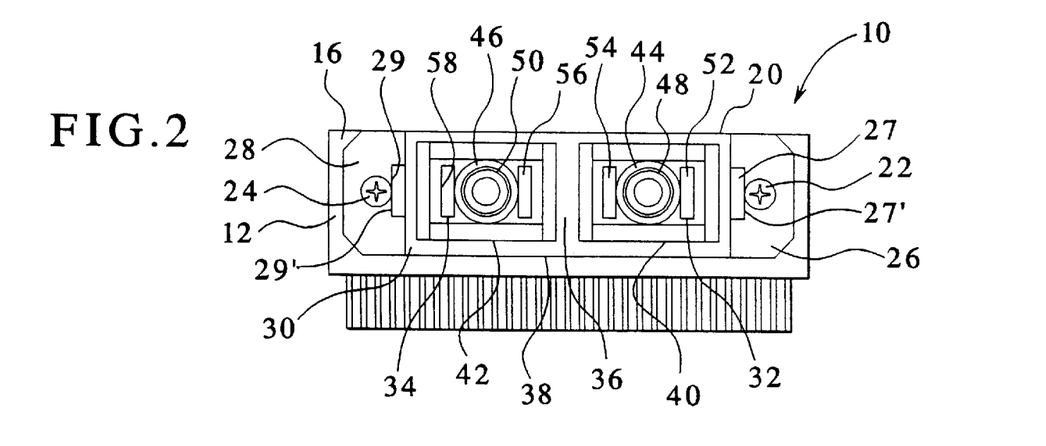
FIG. 2 is a front view of the optoelectronic transceiver module depicted in FIG. 1.

Turning to FIG. 2, a front view of the optoelectronic transceiver module 10 is depicted. The transceiver connector 20 is attached to the first end 16 of the main housing 12 by two screws 22,24. The two screws 22,24 extend through the transceiver connector's mounting ears 26,28 and into the main housing 12. Extending perpendicularly from the mounting ears 26,28 is a generally rectangularly shaped connector shell 30. The connector shell 30 provides two receptacles 32,34 for receiving fiber optic connector plugs. The receptacles 32,34 are formed by the connector shell 30 along with a divider wall 36 which extends along the center of the connector shell. Furthermore, located in the bottom 38 of each receptacle 32,34 is a keying channel 40,42 which extends toward the first end 16 of the main housing.

In the preferred embodiment, the receptacles 32,34 of the connector shell 30 are specifically dimensioned to receive an SC duplex plug. Therefore, the keying channels 40,42 ensure that an SC plug will be inserted so that receptacle 32 will only accept a plug for sending data and receptacle 34 will only accept a plug for receiving data.

Extending from the main housing 12 and into each of the receptacles 32,34 is an optical subassembly 44,46. As previously indicated, the optical subassembly 44 is for sending transmissions over a data link and the optical subassembly 46 is for receiving transmissions over a data link. In order to facilitate the connection between the transceiver 10 and the data links, each optical subassembly has a ferrule receiving portion 48,50. The ferrule receiving portion 48,50 couples with the SC plug. Furthermore, the transceiver's latch members 52,54,56, and 58 firmly hold the SC plug in contact with connector 20.

The actual sending and receiving of optically encoded data is performed by a laser diode within the optical subassembly 44 and a photo diode within the optical subassembly 46. Both the laser diode and the photo diode are electrically connected to a circuit board which is mounted within the main housing 12.

Turning back to FIG. 1, a portion of the circuit board 60 is depicted. Incorporated onto the circuit board 60 is circuitry for transmitting and receiving optically encoded data (circuitry not shown). The circuit board 60 is encased in potting material 62 and a potting box 64 which forms the main housing 12. The potting material 62 encases the circuit board 60 such that only the circuit board's male ribbon style connector 66 extends from the potting material 62.

Figure 3:
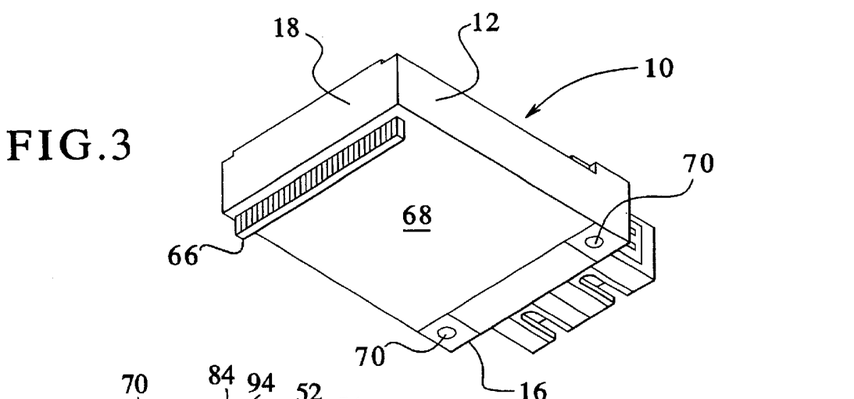
FIG. 3 is a bottom perspective view of the optoelectronic transceiver module depicted in FIG. 1.

Turning to FIG. 3, a perspective view of the bottom 68 of the transceiver module 10 is depicted. In the preferred embodiment, the bottom 68 has two mounting ports 70,70 which are adjacent to the first end 16 of the main housing 12. In addition, the male ribbon style connector 66 protrudes perpendicularly from the bottom 68 and is adjacent to the second end 18 of the main housing 12.

In an alternative embodiment, the ribbon style connector 66 may protrude perpendicularly from the second end 18 of the module 10 so that it can be connected to a circuit card assembly in a direction which is parallel to the direction of insertion of the optic plugs into the module's receptacles. However, in this alternative embodiment, another recess cover will be needed in order to prevent potting material from escaping the second end of the potting box.

Figure 4:
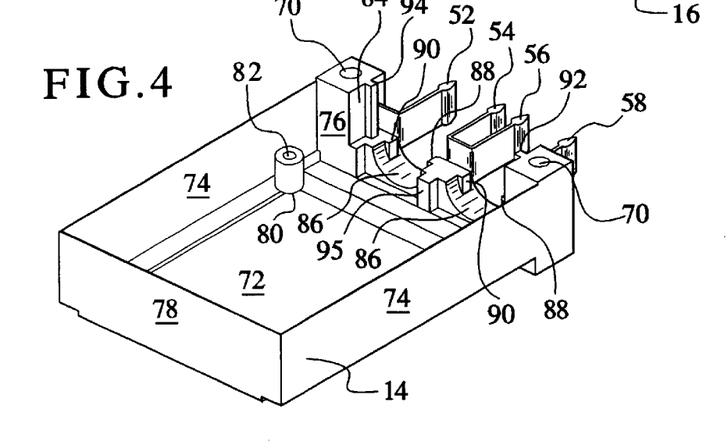
FIG. 4 is an enlarged perspective view of the potting box used in the manufacture of the optoelectronic module depicted in FIGS. 1–3.

Referring to FIG. 4, an enlarged perspective view of the optoelectronic module's potting box 64 is depicted. The potting box 64 forms the outer housing of the optoelectronic module. Thus, the potting box generally has the shape of an oblong box with a rectangular bottom 72, two parallel side walls 74,74, a first end wall 76, and an opposite second end wall 78. In a preferred embodiment, the potting box 64 is injection molded of a polymer material such as VALOX, STANYL, or any other glass-filled heat resistent material which can withstand solder reflow temperatures. The use of such a potting box eliminates the need for a silicone mold required by prior art modules.

In addition, it is preferred that the potting box 64, including the latch members 52,54,56, and 58, be either plated, wet plated, or vacuum metalized with an aluminum or stainless steel coating in order to dissipate an electrostatic discharge and provide for electromagnetic shielding. As well, the transceiver connector 20 (FIG. 1) may be either plated, wet plated, or vacuum metalized, in order to reduce emissions and enhance grounding of the module. Such metalization of the connector 20 can bring the module in compliance with FCC Rules, Part 15. In a preferred embodiment, the connector 20 is metalized separately from the potting box 64 so that each attachment portion is metalized and provides for conductivity between the parts. As the connector 20 will be attached to a chassis containing fiber optic connectors which are at ground potential, the connector will ground the metalized potting box 64 which is attached to a daughter board. Such grounding enhances the module's ability to dissipate electrostatic discharge and provide for electromagnetic shielding.

As also shown in FIGS. 1–3, the transceiver connector 20 includes a grounding clip 25 attached at the slot 23 in the connector 20. The grounding clip 25 serves as a means for forming an electrical connection with an externally grounded structure such as a computer chassis. Correspondingly, the grounding clip 25 is made of a metallic material, such as stainless steel, and includes two tabs 27,29 which protrude from each side of the connector 20. The tabs 27,29 are generally rectangular in shape with only one side of each tab being united to the grounding clip 25. Correspondingly, each tab 27,29 has a respective distal end 27', 29' which extends away from the connector 20. In a preferred embodiment, the connector 20 is first metalized and then the ground clip 25 is attached so that an electrical conductive path is maintained between the grounding clip 25 and the connector 20.

As previously indicated, all of the transceiver's latch members 52, 54, 56, and 58 extend from the first wall 76 of the potting box 64. Also, the first end wall 76 of the potting box furnishes the mounting ports 70,70 which are located on the bottom of the main housing. In a preferred embodiment, the latch members 52, 54, 56 and 58 are integrally molded with the potting box 64.

Circuit board standoff columns 80 are also provided by the potting box 64 (only one standoff column is depicted in FIG. 4). Each standoff column protrudes from the bottom 72 of the potting box 64 and is positioned next to the first end wall 76 and one of the side walls 74,74 for supporting the circuit board 60. The standoff columns 80 have a length equal to approximately half the depth of the potting box 64 with the distal end of the column having a circuit board mounting port 82.

As depicted in FIG. 4, the first wall 76 of the potting box 64 has a recess 84 for allowing the placement of the circuit board's optical subassemblies. The recess 84 has two semicircular through-ports 86,86. Within each through-port 86,86 are two guide beams 88,90 which are positioned on each end of the through-port's semicircle for positioning the optical subassemblies 44,46.

Also located on the first wall 74 are two recess cover alignment guide beams 92,94. The alignment guide beams 92,94 boarder each side of the recess 84 and extend along the entire depth of the recess. The bottom of the recess 84 has three flat mating surfaces 95 (only two of the mating surfaces are depicted in FIG. 4).

Figures 5, 6:
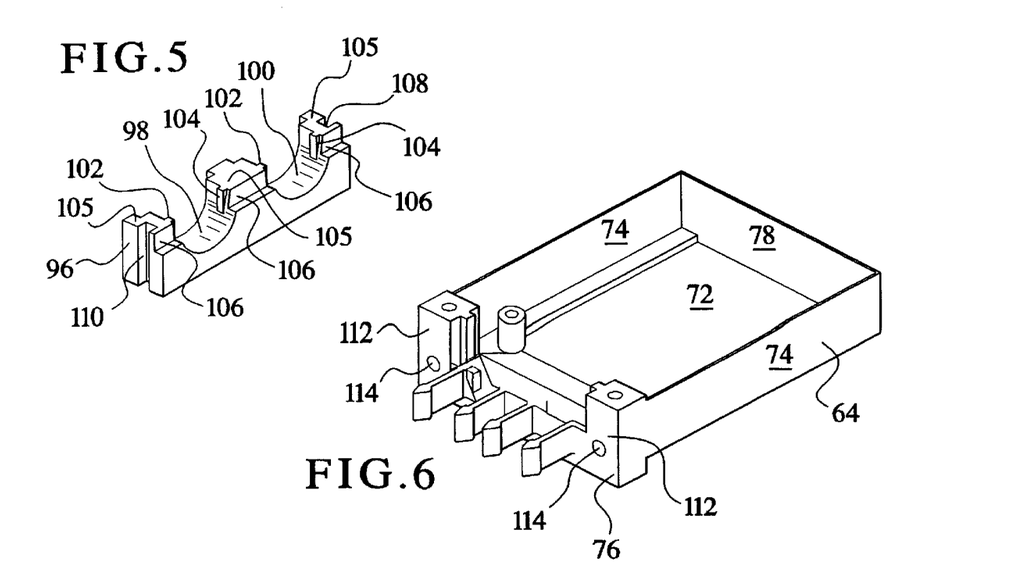
FIG. 5 is a perspective view of the recess cover used with the potting box of FIG. 4.
FIG. 6 is another enlarged perspective view of the potting box of FIG. 4.

Correspondingly, referring to FIG. 5, a recess cover 96 is depicted for placement within the recess located in the first wall of the potting box. Preferably, the recess cover 96 is made of the same material as the potting box and is either plated, wet plated, or vacuum metalized with an aluminum or stainless steel coating.

In FIG. 5, the recess cover 96 has two semicircular through-ports 98,100. Within each of the through-ports 98,100 are two guide beams 102,104 positioned on each end of the through-port's semicircle. Also, the top of the recess cover includes three flat mating surfaces 105.

The recess cover 96 firmly mounts within the recess of the potting box's first wall so that the mating surfaces 95 and 105 of both the recess 84 and the recess cover 96 will abut each other. The recess cover 96 includes three indentions 106 which allow the cover to be positioned around the location where the latch members 52, 54, 56, and 58 attach to the potting box. In addition, on each end of the recess cover 96 there are alignment grooves 108,110 which provide for sliding engagement with the alignment guide beams 92,94 bordering the recess within the potting box's first wall.

Referring back to FIG. 4, during the manufacture of the transceiver module the circuit board is placed in the potting box 64 with the male ribbon connector protruding outside of the potting box and the circuit board's optical subassemblies protruding out of the recess 84 in the first wall 76. The optical subassemblies 44,46 are properly positioned within the potting box 64 by the alignment guides 88,90 located within each through-port 86,86.

Once positioned within the potting box 64, the circuit board 60 is affixed by two screws which are mounted to the standoff columns 80 via the circuit board mounting ports 82.

Once the circuit board 60 is secured within the potting box 64, the recess cover 96 is mounted onto the first end wall 76. The recess cover 96 is mounted by engaging its alignment grooves 108,110 with the potting box's recess cover alignment guide beams 92,94. When the recess cover 96 is slid into position, the cover's through-ports 98,100 and associated alignment guide beams 102,104 will adjoin the circuit board's optical subassemblies 44,46. Furthermore, due to the tight tolerances of both the potting box 64 and the recess cover 96, a liquid tight seal will be formed between the potting box 64, the recess cover 96, and the optical subassemblies 44,46. Thus, with the recess cover 96 in place, potting material is injected within the potting box 64 for encasing the circuit board 60. The time to mold the module by the above method is reduced by approximately 90% over the prior art molding process because no hand caulking is needed to form the liquid tight seal.

Finally, referring to FIG. 6, the connector shell 20 (See FIGS. 1 & 2) is mounted onto the first end wall 76 of the potting box 64 after the potting material has cured. Alignment of the connector shell 20 is provided by two mounting posts 112,112. Each mounting post 112 has a bore 114 which facilitates the attachment of the connector shell 20, by the use of the previously mentioned screws, onto the potting box 64.

In an alternative embodiment, the ribbon style connector 66 may protrude perpendicularly from the second end 18 of the module 10 so that it can be connected to a circuit card assembly in a direction which is parallel to the direction of insertion of the optic plugs into the module's receptacles. However, in this alternative embodiment, another recess cover will be needed in order to prevent potting material from escaping the second end of the potting box.

Referring back to FIG. 1, the male ribbon style connector 66 protruding from the module 10 has a beam portion 116, made of insulative material, which extends perpendicularly across the length of the circuit board 60. The male ribbon style connector 66 also has a first side 118, an opposite second side 120, and a distal end 122. Extending perpendicularly from the circuit board 60 on both the first side 118 and the second side 120 of the male ribbon style connector 66 are twenty-eight electrical contacts 124. Each electrical contact 124 consists of a strip of conductive material which is affixed to the male ribbon style connector 66 and is electrically connected to the circuitry mounted on the circuit board 60.

Figure 7:
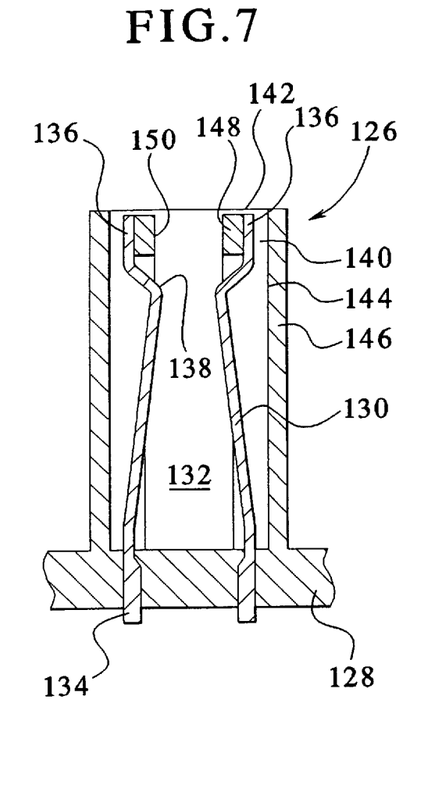
FIG. 7 is an enlarged cut-away side view of the female ribbon style connector taken along line 7—7 of FIG. 1.

Correspondingly, the male ribbon style connector 66 couples to a female ribbon style connector 126 which is mounted onto the circuit card assembly 128. Referring to FIG. 7, an enlarged cut-away side view is shown of the female ribbon style connector 126 taken along line 7—7 of FIG. 1. The female ribbon style connector 126 has two parallel rows of twenty-eight (28) contact beams 130,130 contained within a contact chamber 132 (only one contact from each row is depicted). Each contact beam 130 is constructed of a flat strip of conductive metallic material. Furthermore, each contact beam 130 has a first end 134, a second distal end 136, and a bend 138 which is located adjacent to the second end and extends toward the contact beam located in the opposite row.

The female ribbon style connector 126 is mounted onto the circuit card 128 such that the first end 134 of each contact beam 130 extends through the circuit card assembly. Likewise, the second end 136 of each contact beam 130 extends within a travel limitation slot 140 formed in the top 142 of the female ribbon style connector 126. Each slot 140 provides a backstop 144, consisting of one of the connector's walls 146, and a frontstop 148. Correspondingly, contact beams 130,130 are positioned in the chamber 132 such that the second end 136 of each contact beam 130 resiliently urges against the frontstop 148.

In order to provide access to the contact beams 130,130 within the female ribbon style connector 126, the top 142 of the connector has a slot 150 positioned between the two rows of contact beams. Correspondingly, in order to make an electrical connection between the female ribbon style connector 126 and the male ribbon style connector 166 depicted in FIG. 1, the distal end 122 of the male ribbon style connector is inserted within the female connector's slot 150. As the male ribbon style connector 66 is pushed further within the female connector's chamber 132 the two rows of contact beams 130,130 will be forced to separate further from each other. In addition, each contact beam 130 will resiliently urge against a corresponding electrical contact 124 mounted on the male ribbon style connector 66. Thus, an electrical connection will be formed between the male ribbon style connector's electrical contacts 124,124 and the female connector's contact beams 130,130.

Similarly, to disconnect the male ribbon style connector's electrical contacts 124,124 from the female connector's contact beams 130,130 the male connector 66 is simply pulled from the chamber 132 of the female connector. Once the male ribbon style connector 66 has been removed from the chamber 132, the contact beams 130 of the female connector 126 will resiliently regain the configuration of FIG. 7, whereby the second end 136 of each contact beam will abut its corresponding frontstop 148.

Figure 8:
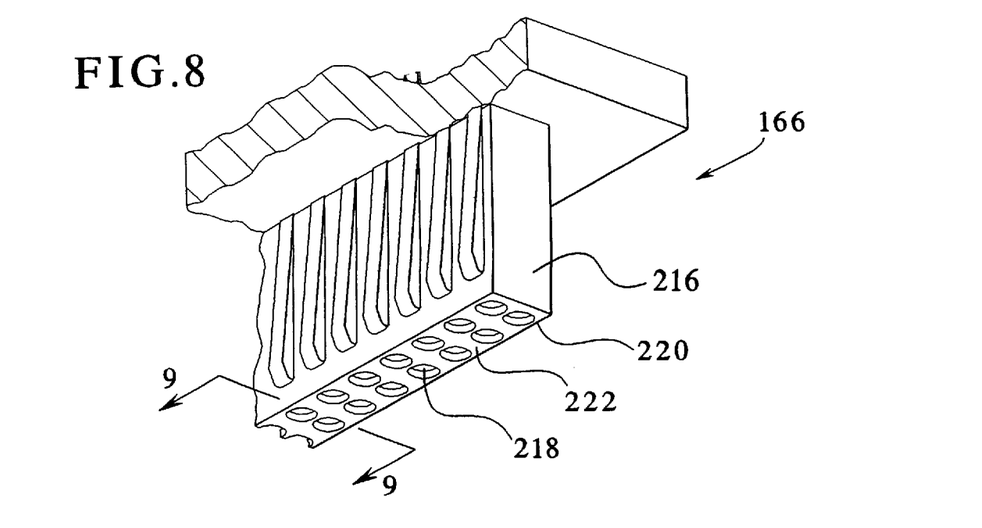
FIG. 8 is an enlarged perspective view, along with a partial fragmentary view, of a resilient male ribbon style connector for use with the optoelectronic transceiver module of FIGS. 1–3.

Turning to FIG. 8, an enlarged perspective view, along with a partial fragmentary view, is depicted of a resilient male ribbon style connector 166. The connector 166 includes a beam type housing 216 having a first side 218, an opposite second side 220, and a distal end 222. The resilient male ribbon style connector 166 in FIG. 8 serves as another embodiment of the male ribbon style connector depicted in FIGS. 1–3 wherein the male connector in FIG. 8 is resilient and the male connector in FIGS. 1–3 is non-resilient. It should be noted, however, that other means for quickly installing and replacing the module from a circuit card assembly may be used.

Figure 9:
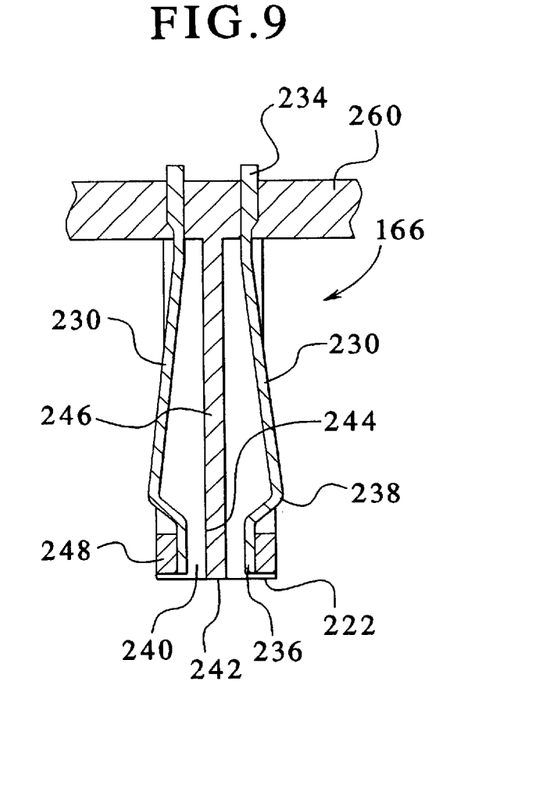
FIG. 9 is a cut-away side view of the resilient male ribbon style connector taken along line 9—9 of FIG. 8.

Referring to FIG. 9, an enlarged cut-away side view of the resilient male ribbon style connector 166 is shown taken along line 9—9 of FIG. 8. The male ribbon style connector 166 has two parallel rows of twenty-eight (28) contact beams 230,230 (only one contact from each row is depicted). Each contact beam 230 is constructed of a flat strip of conductive metallic material. Furthermore, each contact beam 230 has a first end 234, a second distal end 236, and a bend 238 which is located adjacent to the second end and extends away from the contact beam located in the opposite row.

The male ribbon style connector 166 is mounted onto the module's circuit board 260 such that the first end 234 of each contact beam 230 extends through the circuit board. In a preferred embodiment, the first end 234 of the contact 230 is inserted within a through-hole of the circuit board 260 which contains traces for providing an electrical connection from the contact 260 to components mounted on the board. Likewise, the second end 236 of each contact beam 230 extends within a travel limitation slot 240 formed in the top 242 of the resilient male ribbon style connector 166. Each slot 240 provides a backstop 244, consisting of the connector's support wall 246, and a frontstop 248. Correspondingly, contact beams 230,230 are positioned such that the second end 236 of each contact beam 230 resiliently urges against the frontstop 248.

Access for making an electrical connection with the contact beams 230,230 is provided since they protrude from the male ribbon style connector 166 in the area around the bends 238,238. Correspondingly, in order to make an electrical connection between a female ribbon style connector and the resilient male ribbon style connector 166, the distal end 222 of the male ribbon style connector is inserted within a slot provided by the female connector. As the male ribbon style connector 166 is pushed within the female connector, the two rows of contact beams 230,230 will be forced to compress towards each other. In addition, each contact beam 230 will resiliently urge against a corresponding electrical contact mounted within the female ribbon style connector. Thus, an electrical connection will be formed between the male ribbon style connector's electrical contact beams 230, 230 and the female connector's contact beams.

Similarly, to disconnect the resilient male ribbon style connector 166 from the female connector, the male connector is simply pulled from the female connector. Once the male ribbon style connector 166 has been removed, the contact beams 230,230 will resiliently regain the configuration of FIG. 9, whereby the second end 236 of each contact beam will abut its corresponding frontstop 248.

Figure 10:
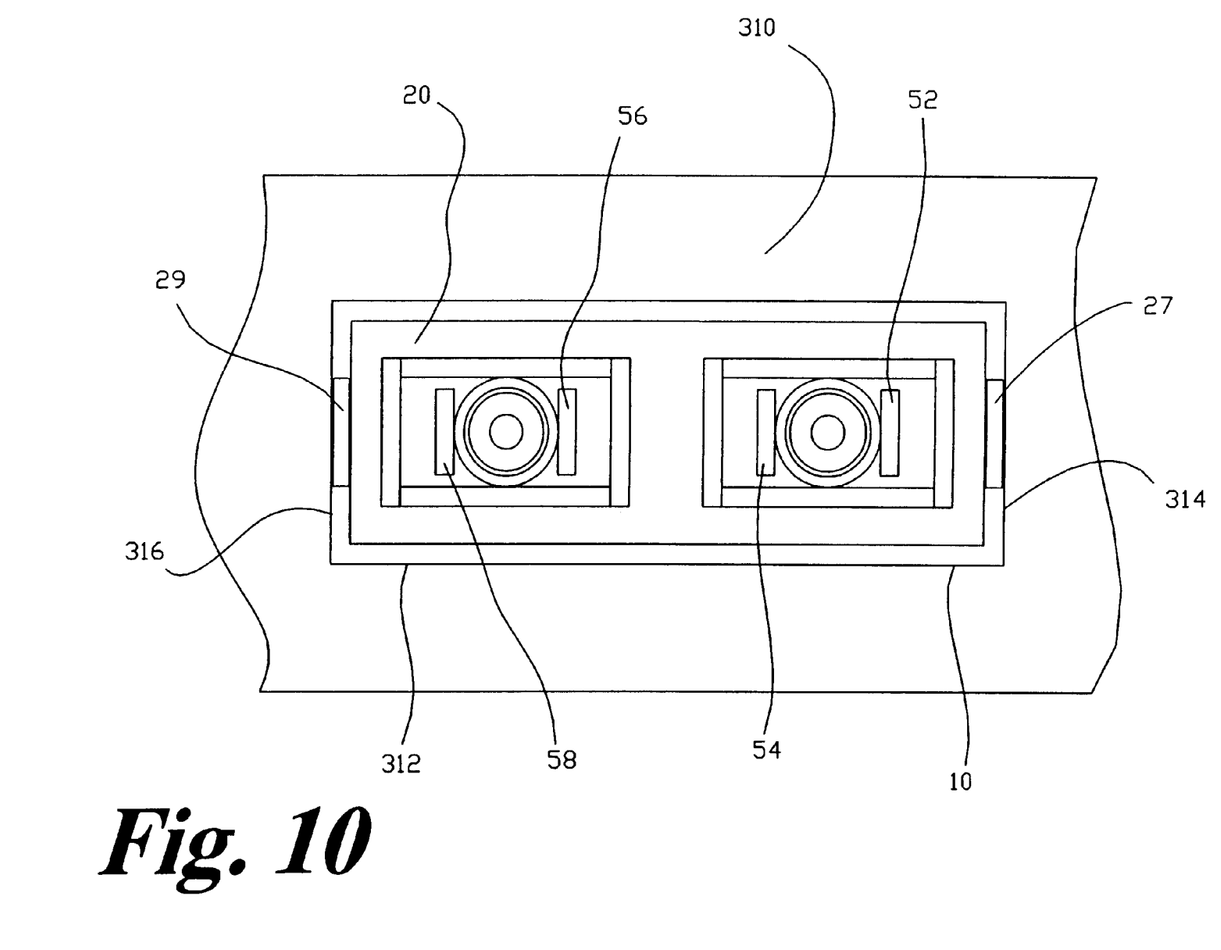
FIG. 10 is a front view of a grounded computer chassis with the optoelectronic transceiver module of FIG. 2 extending through a connector port within the computer chassis.

Moving to FIG. 10, a front view of the outside of a grounded computer chassis 310 is depicted with the connector 20 of the optoelectronic transceiver module 10 extending through a connector port 312 within the computer chassis. As commonly known in the art, the computer chassis 310 is typically made of a conductive metallic material and is tied to a ground potential (i.e., grounded) by conventional means. Furthermore, the chassis provides a connector port 312 for each optoelectronic transceiver module mounted within the computer chassis (only one connector port and one transceiver module is depicted in FIG. 10). As shown in FIG. 10, the connector port 312 consists of an opening which is dimensioned so that the transceiver module connector 20 can extend through the connector port. Therefore, the transceiver module 10 can be mounted within the chassis 310 of a computer with the transceiver module connector 20 extending from, and being readily accessible from, the outside of the computer chassis.

Correspondingly, when the transceiver module connector 20 is positioned within the connector port 312, the tabs 27,29 will press against the sides 314,316 of the connector port. Consequently, the tabs 27,29 will form an electrical connection with the computer chassis which will result in the transceiver module connector 20 becoming grounded. In addition, the entire metalized potting box, including the metalized latch members 52,54,56, and 58, will become grounded since, as indicated previously, the transceiver module connector 20 is conductively attached to the potting box.

Correspondingly, a means of pre-grounding an SC connector is provided by the grounded latch members 52,54,56, and 58. For example, as an SC connector is attached to the transceiver module 10, the housing of the SC connector will first abut against one of the ground latch members 52,54,56, and/or 58. Accordingly, any static charge on the SC connector will be removed by the grounded latched members via the conductive electrical path from the potting box, to the transceiver connector, its corresponding grounding clip, and then to the grounded computer chassis via the tabs 27,29. Therefore, the SC connector is pre-grounded before it is connected to the electronics within the transceiver module.

Although, the preferred embodiment of pre-grounding an optical connector describes a transceiver module which consists of a metalized potting box with metalized latches, it should be understood that the above invention extends to any type of optoelectronic module, such an a GLM module, which has latches for mating with a fiber optic connecter including, but not limited to, an SC connector. Correspondingly, the latches of a transceiver module, such as a GLM module, must be metalized in order to provide an electrically conductive path to the grounded computer chassis.

Furthermore, although a grounding clip having tabs was used in the preferred embodiment of the present invention to form an electrical connection with the grounded computer chassis, it should be understood by those skilled in the art that other alternative structures can be substituted for the grounding clip, such as, for example, a conductive cable which can be connected to both the computer chassis and the metalized potting box or its connector. Further, although a preferred embodiment of the inventions is an optoelectronic transceiver, any transceiver may use the features of the present invention, such as a transceiver transfers data over a copper wire/medium.

In addition, it should be understood that in describing the top and bottom portions of the transceiver module and its respective potting box components, the terms "top" and "bottom" are used by way of example only due to the orientation of the drawings. It should also be understood that various changes and modifications to the presently preferred embodiments described herein will be apparent to those skilled in the art. Furthermore, although the transceiver module depicted in the presently preferred embodiment has its male ribbon style connector extending from the bottom, it should be understood from the outset that the connector can be configured to extend, for example, from the second end of the transceiver. Therefore, changes and modifications may be made without departing from the spirit and scope of the present invention and without diminishing its attendant advantages. Thus, it is intended that such changes and modifications be covered by the appended claims.

We claim:

1. An electromagnetically shielded host system comprising:

a grounded chassis including a metallic faceplate having a rectangular connector port; and an optoelectronic module mounted in said at least one connector port so that a gap is provided between the module and the faceplate, the module including a first end having at least one rectangular duplex metallic optical connector, the module including a second end having electrical contacts protruding therefrom to connect the module to a motherboard and wherein a compliant grounding member is adapted to resiliently occupy the gap and provide mechanical and electrical connection to the faceplate of the chassis so that a portion of the module can achieve a ground potential approximately equal to that of the faceplate in order to enhance electromagnetic shielding and to reduce electromagnetic radiation from leaking from the host system.

2. The host system of claim 1 wherein the faceplate includes an abutment surface that abuttingly contacts the compliant grounding member in order to provide the mechanical and electrical connection to the faceplate.

3. The host system of claim 2 wherein the gap is adjacent the abutment surface and the compliant grounding member electrically connects the abutment surface and the metallic optical connector.

4. The host system of claim 1 wherein the metallic optical connector includes a divider wall having a conductive portion and the divider wall separating a pair of optical receptacles.

5. The host system of claim 4 wherein the abutment surface is electrically connected to the divider wall of the optical connector.

6. The host system of claim 1 wherein the compliant grounding member comprises a metallic ground clip attached to the first end of said module.

7. The host system of claim 6 wherein the ground clip abuts against the connector port in order to provide the mechanical and electrical connection to the faceplate and provide the portion of the module at ground potential.

8. The host system of claim 7 wherein the ground clip includes a tab that abuts against the faceplate.

9. The host system of claim 7 wherein the module includes an optical connector including a metallized portion.

10. The host system of claim 7 wherein the entire optoelectronic module housing is metallic and is grounded to the faceplate via the ground clip.

11. The host system of claim 7 wherein the housing is metallized.

12. The host system of claim 7 wherein the optical connector is metallized.

13. The host system of claim 7 wherein the optical connector is an SC duplex receptacle.

14. The host system of claim 7 where in the optical connector includes a push/pull connector system.

15. The host system of claim 7 wherein the module includes an optical subassembly.

16. The host system of claim 7 wherein the module includes a male ribbon style connector at a second end.

17. The host system of claim 7 wherein the ground clip includes a resilient contact finger protruding therefrom and upon the insertion of the module through the faceplate the resilient contact finger is depressed and mechanically and electrically connects the faceplate to the metallic portion of the module.

18. The host system of claim 1 wherein the faceplate includes an abutment surface that connects to a divider wall of the optical connector.

19. An optoelectronic module for mounting within an electromagnetically shielded host system including a metallic faceplate having a connector port, wherein a gap is formed between the module and metallic faceplate, the module comprising:

a housing having a metallic surface;

a first end having a duplex optical connector;

a second end having electrical contacts protruding therefrom to connect the module to a motherboard;

a ground member adapted to resiliently occupy the gap and provide a mechanical and electrical connection between the faceplate of the host system and the metallic surface of the module housing so that the metallic surface of the housing of the module achieves a ground potential approximately equal to that of the faceplate in order to enhance electromagnetic shielding and to reduce electromagnetic radiation from leaking from the host system.

20. The module of claim 19 wherein the ground member is sized to resiliently occupy only a portion of the gap when the gap extends about a periphery of the first end.

21. The module of claim 19 wherein the ground member includes a tab located at the first end and adapted to occupy a portion of the gap in order to divide an opening of the connector port.

22. The optoelectronic module of claim 19 wherein the ground member comprises a compliant metallic ground clip attached to first end of said module.

23. The optoelectronic module of claim 19 wherein the ground member comprises a metallic ground clip incorporated with the first end of said module.

24. The optoelectronic module of claim 19 wherein the ground member is a separate member from the first end of the module.

25. The optoelectronic module of claim 19 wherein the ground member includes a resilient contact finger protruding therefrom and upon the insertion of the module through the faceplate the resilient contact finger is depressed and mechanically and electrically connects the faceplate to the metallic portion of the module.

26. The optoelectronic module of claim 19 wherein the faceplate includes an abutment surface that connects to a divider wall of the optical connector.

27. The optoelectronic module of claim 19 wherein the entire optoelectronic module housing is metallic and is grounded to the faceplate via the ground member.

28. An optoelectronic module for mounting within an electromagnetically shielded host system including a metallic faceplate having a connector port port wherein a gap is formed between the module and metallic faceplate, the module comprising:

a housing having a metallic surface;

a first end having a transceiver connector having a receptacle opening configured for receiving a push/pull type optical connector;

a second end having electrical contacts protruding therefrom to connect the module to a motherboard;

a ground member adapted to resiliently occupy the gap and provide a mechanical and electrical connection between the faceplate of the host system and the metallic surface of the module housing so that a portion of the module achieves a ground potential approximately equal to that of the faceplate in order to enhance electromagnetic shielding and to reduce electromagnetic radiation from leaking from the host system.

29. The optoelectronic module of claim 28 wherein the transceiver connector includes the metallic surface thereon and the ground member electrically connecting the transceiver connector to the faceplate.

30. The optoelectronic module of claim 29 wherein the metallic surface of the transceiver connector is electrically connected to a metallic portion of the housing and the ground member electrically connecting the housing to the faceplate and providing the housing at approximately the same ground potential as the faceplate.

31. The optoelectronic module of claim 28 wherein the transceiver connector includes an SC duplex style receptacle for receiving an SC duplex style fiber optic plug therein.

32. The optoelectronic module of claim 28 wherein the ground member includes a ground clip.

33. The optoelectronic module of claim 32 wherein the ground clip surrounds the first end of the module.

34. The optoelectronic module of claim 28 wherein the ground member includes a resilient contact finger and upon insertion of the module through the faceplate the resilient contact finger is depressed and mechanically and electrically connects the faceplate to the metallic portion of the module.

35. The optoelectronic module of claim 28 wherein the faceplate includes an abutment surface that connects to a divider wall of the transceiver connector.

* * * * *